United States Patent [19]

Weigert

[11] 4,200,108
[45] Apr. 29, 1980

[54] ELECTROMEDICAL APPARATUS

[75] Inventor: Kurt Weigert, Nuremberg, Fed. Rep. of Germany

[73] Assignee: Siemens Aktiengesellschaft, Berlin & Munich, Fed. Rep. of Germany

[21] Appl. No.: 953,366

[22] Filed: Oct. 23, 1978

[30] Foreign Application Priority Data

Nov. 7, 1977 [DE] Fed. Rep. of Germany ....... 2749792

[51] Int. Cl.$^2$ ............................................. A61N 1/36
[52] U.S. Cl. ............................................. 128/419 R
[58] Field of Search .................... 128/419 R, 420, 421, 128/422, 423

[56] References Cited

U.S. PATENT DOCUMENTS

| | | | |
|---|---|---|---|
| 3,489,152 | 1/1970 | Barbara | 128/422 |
| 4,068,669 | 1/1978 | Niemi | 128/419 R |
| 4,088,141 | 5/1978 | Niemi | 128/421 |
| 4,102,347 | 7/1978 | Yukl | 128/421 |
| 4,126,137 | 11/1978 | Archibald | 128/422 |
| 4,141,359 | 2/1970 | Jacobson et al. | 128/419 R |

*Primary Examiner*—William E. Kamm
*Attorney, Agent, or Firm*—Hill, Van Santen, Steadman, Chiara & Simpson

[57] ABSTRACT

Known current stimulation apparatus have a current waveform generator with a constant-current output stage, which operates with a relatively high operating voltage (up to several 100 Volts), in order that the necessary currents can be applied even in the case of extremely high patient resistances. In the application of large-surface electrodes, the load resistances are generally comparatively low. The operating voltage required for the necessary currents for such normal instances is here substantially lower than the high operating voltage actually available, which leads to unpleasant irritation phenomena due to an increase in the current density when the resistance is suddenly altered due to the separation of the electrodes or the like. In accordance with the illustrated embodiment, the constant-current stage and the operating voltage supply are connected to an operating voltage control circuit which, in dependence upon the load resistance and/or the current intensity, regulates the operating voltage ($U_B$) for the constant current stage from an initial voltage value ($U_V$) to higher values with an increasing load resistance, whereby, however, the control time constant is such that, in the case of a differential resistance change which exceeds a specifiable threshold, the change in the operating voltage proceeds less rapidly than the resistance change. In the case of rapid change, for example, due to the separation and falling-off of electrodes, the operating voltage is thus only slowly adjusted upwardly such that undesired irritation pheomena are prevented.

10 Claims, 1 Drawing Figure

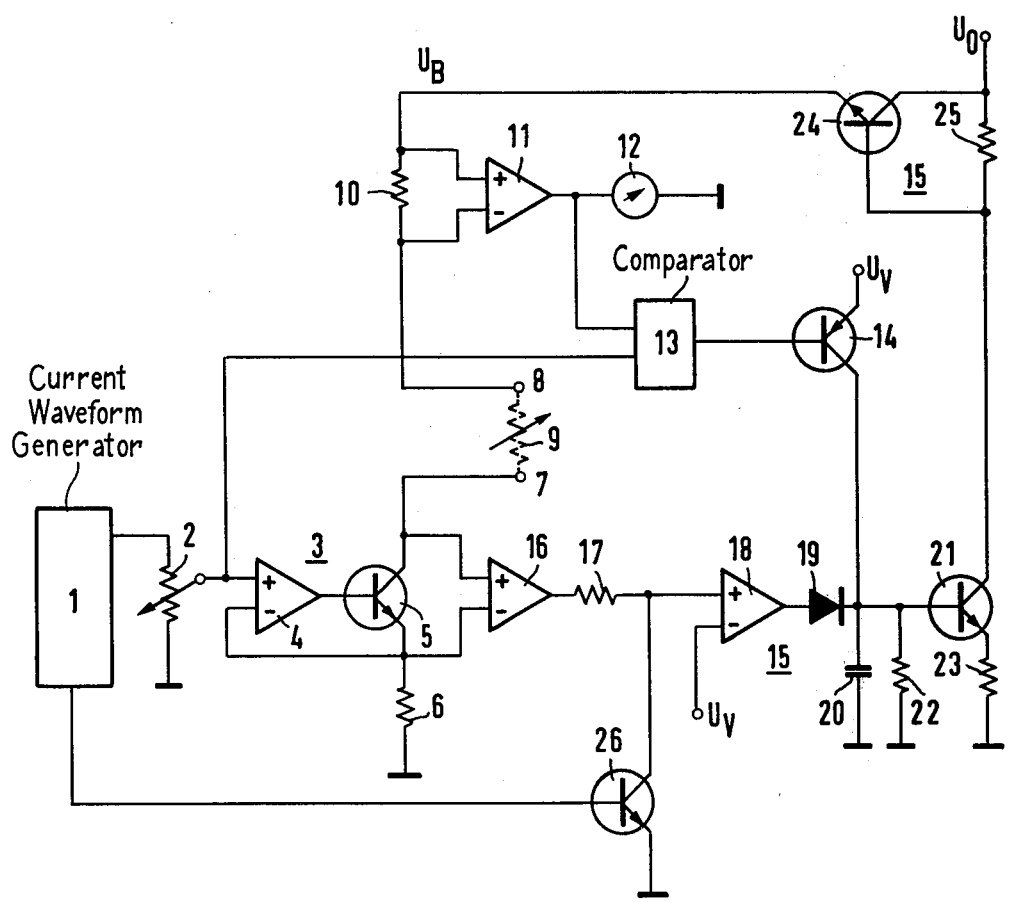

ELECTROMEDICAL APPARATUS

BACKGROUND OF THE INVENTION

The invention relates to an electromedical apparatus, particularly a stimulation current apparatus comprising a current waveform generator as well as a constant current stage for controlling the output current through a load resistance, preferably the human body of a patient, which functions with a specifiable operating voltage.

Known apparatus of this type, particularly electromedical stimulation apparatus, have a constant current output stage which operates with a relatively high operating voltage (up to several 100 V). This is intended to guarantee that, even in the case of extremely high patient resistances, the currents necessary for therapy or diagnosis, respectively, can be applied with the correspondingly high operating voltage requirement. In the case of a conventional method of treatment, the patient resistances are indeed relatively low (e.g. in the case of application of large-surface electrodes); thus, during application in these normal cases, an operating voltage is needed for the required currents which lies substantially lower than the high operating voltage available. This discrepancy leads to very unpleasant occurrences in those instances when e.g. the patient resistance is suddenly varied; this particularly applies to the instance in which the current supply electrodes have become disengaged at the application location and have finally completely dropped off. At the moment of detachment, namely, the area of current passage becomes rapidly reduced such that, in conjunction with the characteristic of a constant current source, the current density on the skin takes on very high values at the application location. This leads to a very unpleasant, painful irritation of the patient treated. In many instances, also, direct burns of the skin are brought about as a consequence. If the supply electrodes have finally completely dropped off, the full, dangerously high operating voltage is connected between the electrodes as long as the apparatus is still in operation and continues to function with the previously set intensity.

SUMMARY OF THE INVENTION

In an electromedical apparatus of the type initially cited, it is the object of the present invention to ensure that unpleasant current - or voltage - effects are avoided with certainty in the case of a sudden deviation from the normal operating conditions. In particular, in the case of stimulation current apparatus, the occurrence of unpleasant or even dangerous irritations is to be prevented when the current supply electrodes become detached and drop off. In addition, the dropped-off electrodes are to be prevented from carrying the high operating voltage.

In accordance with the invention, the object is achieved by virtue of the fact that the constant current stage and the operating voltage supply are connected to an operating voltage control circuit which regulates the operating voltage, in dependence upon the load resistance and/or current intensity, from an initial voltage value at an initial intensity, preferably zero, to higher values with an increasing load resistance, whereby, however, the control time constant of the operating voltage control circuit is matched relative to the differential resistance change of the load resistance such that, in the case of a differential resistance change which exceeds a specifiable threshold, the change in the operating voltage proceeds less rapidly than the resistance change, as a consequence of which the voltage control circuit is switched to a lower operating voltage value, preferably to the initial voltage value of the operating voltage.

In the apparatus in accordance with the invention, in the normal case, there is always a relatively low operating voltage connected to the load resistance; for example, the patient during stimulation current treatment. Only when the patient resistance increases or e.g. the intensity is adjusted upwardly, does the operating voltage automatically adapt itself correspondingly to the higher required value. As long as a change of the cited magnitudes proceeds relatively slowly, the operating voltage follows these changes in direct proportionality. However, if the change proceeds very rapidly—which is e.g. the case when the electrodes become detached and drop off or if there are very rapid intensity changes—the operating voltage is upwardly adjusted only very slowly. Due to the changeover switching to the lower operating voltage value which then takes place, unpleasantly high current densities are prevented and, in the case of dropping-off of the electrodes, only the low operating voltage value is then still connected to these electrodes. As already indicated, unpleasant irritations can also be brought about through a too rapid upward adjustment of the current intensity by means of an intensity adjustment member. Thus, in an advantageous further development of the invention, even in such a case wherein the current intensity change takes place with a rate exceeding a specifiable threshold, the change of the operating voltage by means of the operating voltage control circuit should proceed with a greater time constant than the differential voltage change via the load resistance. In this specific instance, precisely the same effect occurs as, for example, during the detachment and subsequent dropping-off of electrodes; i.e., the operating voltage value, just as in the above instance, is switched to a lower value.

Further advantages and details of the invention are apparent from the following description of a sample embodiment on the basis of the drawing in conjunction with the subclaims; and other objects, features and advantages will be apparent from this detailed disclosure and from the appended claims.

BRIEF DESCRIPTION OF THE DRAWING

The single FIGURE illustrates an electromedical stimulation current apparatus as a sample embodiment of the invention in a basic circuit diagram.

DETAILED DESCRIPTION

In the basic circuit diagram, 1 designates a current waveform generator for stimulation currents to be selected. Current waveform generator 1 is connected via a current intensity adjustment member 2 (potentiometer), with a constant current stage 3 which consists, in a conventional manner, of a voltage amplifier 4, transistor 5, and transistor-emitter-resistance 6. As indicated by broken lines, the variable patient resistance 9 is connected between the current supply electrodes 7 and 8. The operating voltage for the patient circuit is referenced with $U_B$. In addition, there is disposed in the patient circuit a measuring resistance 10 for the actual value of the patient current which is connected via an amplifier stage 11 to a display unit 12 for indicating the actual value of the patient current, on the one hand, and which is connected to a comparator input of a comparator 13, on the other hand. The respective nominal value of the current intensity, which is determined by the output voltage of the intensity adjustment member 2, is connected to the other comparator input of comparator 13. In the case of deviations between the actual and nominal values, comparator 13 generates an output signal which switches transistor 14 into the conductive state, as a consequence of which a relatively low voltage $U_V$ ($U_V$ may be approximately 10 to 20 V) is connected, in the illustrated manner, into the functional circuit of an operating voltage control unit 15. The operating voltage control unit 15 comprises a voltage amplifier 16 for a voltage tapped via the collector-emitter-path of the transistor 5 in the constant current stage 3. It comprises, in addition, the resistance 17, connected to the output side, as well as a voltage adjustment member 18 (operational amplifier) to which a comparison voltage $U_V$ is connected (which in the present sample embodiment is equal to the voltage $U_V$ of transistor 14). Voltage amplifier 18 is followed, via a diode 19 at the coupling point of transistor 14, by a storage capacitance 20 with a succeeding first control transistor 21 which is wired with resistances 22 and 23. Transistor 21 is followed by a second control transistor 24 with the wiring resistance 25. Control transistor 24 is connected at its collector-end to the DC voltage supply $U_O$. In the operating voltage control circuit 15, in addition, there is arranged before voltage adjustment member 18 an additional switching transistor 26 which connects, in dependence upon the current waveform of the current generator 1, to the voltage adjustment member 18 voltage signals from the constant current stage 3 only when current maxima occur in the load circuit.

The method of operation of the basic circuit is as follows:

Given zero intensity at intensity adjustment member 2, the control of the operating voltage $U_B$ proceeds via operating voltage control circuit 15 such that the operating voltage value $U_B$ is adjusted to the relatively low operating value $U_B$ ($U_V$) corresponding to the value $U_V$ of the comparison voltage of the voltage adjustment member 18. If, in the case of applied electrodes 7 and 8, the intensity of the stimulation current in the patient circuit is slowly adjusted upwardly for the case of a specified patient resistance 9, the voltage across the patient resistance increases, whereas the voltage drop across transistor 5 is slowly reduced. The slow reduction in the voltage across transistor 5 effects in the operating voltage control circuit 15 a slow control of the operating voltage value $U_B$ to a higher value ($U_B$ greater than the value corresponding to $U_V$). The time constant of the operating voltage control amounts to $\tau = C \cdot R \parallel R_{ET}$, wherein C is the capacitance of the capacitor 20 and $R \parallel R_{ET}$ is the resistance value of the parallel circuit consisting of the resistance 22 with the resistance value R and the input resistance of transistor 21 with resistance value $R_{ET}$. As long as changes in the intensity of the current in the patient circuit proceed very slowly or also as long as the patient resistance itself changes only very slowly, the adaptation of the operating voltage $U_B$ proceeds with approximately the time constant of this change. However, if the change in the current intensity or also the change in the patient resistance exceeds a predetermined rate of change threshold—which is always the case when electrodes 7 or 8, on the patient's body become loosened and drop off, or if the current intensity at the current adjustment member 2 is inadvertently too rapidly increased—the operating voltage $U_B$ is adjusted less rapidly to higher values, by means of the operating voltage control unit 15, than would be required to maintain the corresponding stimulation current. However, there thus also results a disproportion between the actual value of the current in the patient circuit and the nominal value adjusted by means of intensity adjustment unit 2. The actual value drops, since, due to the very rapid increase of the patient resistance, for example, transistor 5 of the constant current stage reaches saturation, as a consequence of which the voltage across transistor 5 drops very rapidly. Since the drop in the voltage across transistor 5 proceeds with a very much smaller time constant than the control time constant of the control circuit 15, the actual value of the patient current decreases on account of the operating voltage $U_B$ following only with a very great delay. The decrease of the actual value; i.e., the deviation from the nominal value, is, however, detected by comparator 13 and responded to with the emission of a switching signal for transistor 14. Transistor 14 now connects voltage value $U_V$ to the capacitor 20 of the operating voltage control stage 15, which voltage value $V_V$ corresponds to the initial control voltage value at the zero intensity setting. In this manner, the relatively low operating voltage value $U_B$ ($U_V$) is then automatically adjusted at electrodes 7 and 8. Thus, with the illustrated circuit, it has been made possible that, in the case of detachment and dropping off of the electrodes 7 or 8 from the patient's body 9, the actual value of the stimulation current in the patient circuit decreases very rapidly on account of the very delayed voltage readjustment. In the case of repeated contact of electrodes 7 or 8 with the patient's body prior to dropping off, high current densities during passage onto the skin will with certainty not occur; unpleasant or painful irritations or even burns on the skin are thus avoided. If the electrodes have finally fallen off, the very low and thus also non-dangerous operating voltage value $U_B$ ($U_V$) is then connected to these electrodes, which operating voltage value corresponds to that present in the case of the zero intensity setting. The patient is thus protected from unpleasant effects in the case of electrode loosening or falling off. The same also applies to the instance of an excessively rapid current intensity increase. If, namely, the adjustment member 2 is carelessly adjusted upwardly too rapidly, the same effect will occur as in the case of excessively rapid resistance change. Transistor 5 is rapidly brought to saturation, while the actual value of the current in the patient circuit rapidly drops relative to the setting value at adjustment member 2. Comparator 13 again becomes activated, so that voltage value $U_V$ is connected via transistor 14 into the operating voltage control circuit 15. Thus, also in the case of excessively rapid current increase, the operating voltage value is adjusted to a relatively low value. Thus, also regarded from this point of view, the patient can no longer be burdened or even endangered by excessively high current densities.

It will be apparent that many modifications and variations may be effected without departing from the scope of the novel concepts and teachings of the present invention.

I claim as my invention:

1. Electromedical apparatus, particularly a stimulation current apparatus, comprising a current waveform generator as well as a constant current stage for controlling the output current through a load resistance, preferably the human body of the patient, which operates with a specifiable operating voltage, characterized in an operating voltage control circuit (15), the constant current stage (3) and operating voltage supply ($U_o$) being connected to said operating voltage control circuit (15), said control circuit (15) being operable to adjust the operating voltage ($U_B$) from an initial voltage value at an initial intensity to higher values with an increasing load resistance, said control circuit (15) having a control time constant of such a value relative to the differential resistance change of the load resistance, that, in the case of a differential resistance change exceeding a specifiable threshold, the change of the operating voltage proceeds less rapidly than the resistance change, as a consequence of which the control circuit is switched to a lower operating voltage value.

2. Apparatus according to claim 1, characterized in that, even in the case of a change in current intensity setting at an intensity adjustment member (2) for the constant current stage (3) which exceeds a specifiable threshold in the rate of change of the intensity setting, the change of the operating voltage through the operating voltage control circuit (15) proceeds with a greater time constant than the differential voltage change across the load resistance (9).

3. Apparatus according to claim 1, characterized in that the operating voltage control circuit (15) comprises a voltage adjustment member (18) which, in dependence upon a comparison voltage, controls the operating voltage according to a control voltage value substantially equal to the comparison voltage if the initial intensity value is set at an intensity adjustment member (2) for the constant current stage (3), and that this control voltage value produces substantially the initial voltage value of the operating voltage ($U_B$).

4. Apparatus according to claim 3, characterized in that, in the case of voltage drop at the voltage adjustment member (18) of the operating voltage control circuit (15), which is brought about either by a current intensity setting increase or a rise in the load resistance, the operating voltage is adjusted by the operating voltage control circuit (15) to higher values.

5. Apparatus according to claim 3, characterized in that the variable input voltage for the voltage adjustment member (18), which serves as a criterion for changes in the load resistance or in the adjustment of the current intensity, is tapped via a current regulating member (5), which is a component part of the current constant stage (3).

6. Apparatus according to claim 1, characterized in that a comparator (13) is allocated to the circuit for the load resistance (9) as well as to a current intensity adjustment member (2), which comparator (13) compares the actual value of the current, tapped in the circuit for the load resistance, with an adjusted nominal value, and, when the actual value falls, below the nominal value, adjusts the operating voltage control circuit (15) in such a manner that, through the latter, the operating voltage value is set to a low value.

7. Apparatus according to claim 6, characterized in that the actual value of the current through the load resistance is tapped by means of a measuring resistance (10) in the circuit for the load resistance.

8. Apparatus according to claim 6, characterized in that a voltage ($U_V$) is capable of being connected to an output capacitor (20) for the voltage adjustment member (18) in the operating voltage control circuit (15) by means of a switching member (14) when, at the comparator (13), the actual value of the current in the load circuit falls below the nominal value, whereby the voltage to be connected corresponds at least to the control voltage value supplied by the voltage adjustment member (18), or is greater than the latter, and whereby the connection of this voltage ($U_V$) proceeds pursuant to a simultaneous decoupling of the voltage adjustment member (18) from the output capacitor (20).

9. Apparatus according to claim 8, characterized in that a diode (19) serves the purpose of decoupling and is blocked in the case of voltages at the output capacitor which are greater in amount than an output voltage at the voltage adjustment member (18).

10. Apparatus according to claim 1, characterized in that a switching member (26) is arranged in the operating voltage control circuit (15), which switching member (26), in dependence upon the current waveform of the current generator (1), connects to a control voltage from the current constant stage (3) only when current maxima occur in the load current.

* * * * *